United States Patent [19]

Pesson

[11] 4,292,317
[45] Sep. 29, 1981

[54] 1,4-DIHYDRO-QUINOLINE-3-CARBOXYLIC ACID DERIVATIVES, PROCESS FOR THEIR PREPARATION AND COMPOSITIONS CONTAINING THEM

[75] Inventor: Marcel Pesson, Paris, France

[73] Assignees: Laboratorie Roger Bellon, France; Dainippon Pharmaceutical, Japan

[21] Appl. No.: 942,635

[22] Filed: Sep. 15, 1978

[30] Foreign Application Priority Data

Sep. 20, 1977 [GB] United Kingdom ............... 39197/77
Apr. 3, 1978 [GB] United Kingdom ...... 12983/78
May 30, 1978 [GB] United Kingdom ... 39197/12983/78

[51] Int. Cl.$^3$ .................. A61K 31/495; C07D 401/04
[52] U.S. Cl. ............................... 424/250; 424/248.53; 424/258; 544/128; 544/363; 546/156
[58] Field of Search .................. 544/363; 424/250

[56] References Cited
U.S. PATENT DOCUMENTS 4,017,622  4/1977  Minami et al. ....................... 544/363
4,146,719  3/1979  Irikura ................................. 544/363

Primary Examiner—Paul M. Coughlan, Jr.
Attorney, Agent, or Firm—Lewis H. Eslinger

[57] ABSTRACT

New 7-dialkylamino-1-substituted-6-halogeno-4-oxo-1,4-dihydroquinoline-3 carboxylic acids of the formula:

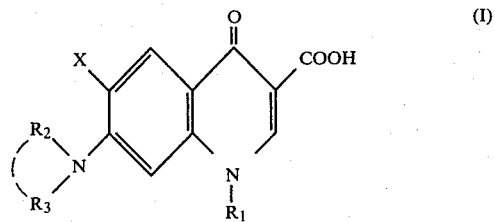

wherein the $R_1$ substituent is methyl, ethyl, vinyl or allyl and non-toxic pharmaceutically acceptable acid addition salts thereof. These compounds are useful as antibacterial agents. Also disclosed are processes for preparing the compounds.

12 Claims, No Drawings

1,4-DIHYDRO-QUINOLINE-3-CARBOXYLIC ACID DERIVATIVES, PROCESS FOR THEIR PREPARATION AND COMPOSITIONS CONTAINING THEM

This invention is concerned with certain novel 1,4-dihydro-quinoline-3-carboxylic acid derivatives, with a process for their preparation, and with compositions containing them.

It is known that 1-alkyl-7-dialkylamino-4-oxo-1,4-dihydro-quinoline-3-carboxylic acids are anti-bacterial agents. Compounds of this type, which have a piperazinyl radical or a 4-substituted piperazinyl radical as the dialkylamino grouping, are described in French Pat. No. 2,210,413. The corresponding compounds which contain a vinyl radical as the 1-substituent have the same properties and form the subject of French Pat. No. 2,257,292.

We have now unexpectedly found that the introduction into the above-mentioned compounds of a halogen atom (in particular chlorine or fluorine) in the 6-position, gives new derivatives which are more active and possess a broader spectrum of antibacterial activity. These halogeno derivatives are active at low concentrations against both Gram positive and Gram negative bacteria and thus constitute valuable agents for the treatment of infectious human or animal diseases. They can also be used as growth factors in animals by addition to their feed.

According to the present invention, therefore, there are provided 6-halogeno-1-substituted-7-disubstituted-amino-4-oxo-1,4-dihydro-quinoline-3-carboxylic acids of formula 1:

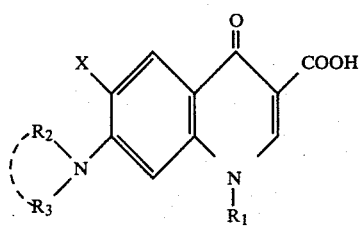

in which $R_1$ is a lower alkyl radical, a lower aralkyl radical, a vinyl or allylradical, a lower hydroxyalkyl radical, or a lower halogeno-alkyl radical, $R_2$ and $R_3$ are each a lower alkyl radical or, together with the nitrogen atom to which they are attached, form a 5- or 6-membered heterocyclic ring containing the nitrogen atom and, optionally, a second nitrogen or oxygen heteroatom, which heterocyclic ring may optionally be substituted, and X is a halogen atom, preferably chlorine, bromine or fluorine.

The term "lower alkyl" means an alkyl radical having 1 to 5, and preferably 1 to 2, carbon atoms.

In particular, $R_1$ is a methyl, ethyl, benzyl, vinyl, allyl, 2-hydroxy ethyl or 2-chloroethyl radical, $R_2$, $R_3$ are each a methyl radical.

When $R_2$ and $R_3$ form a heterocyclic ring, they preferably form a pyrrolidino, piperidino, hydroxypiperidino, morpholino or piperazinyl group, which may be substituted or unsubstituted. A preferred class of heterocyclic groups is that of 4-substituted or non-substituted piperazinyl groups of the formula:

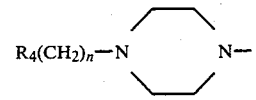

in which n is an integer from 0 to 3, $R_4$ is a hydrogen atom, a hydroxyl group (provided n is 2 or 3), an unsubstituted or substituted phenyl group, a vinyl group (provided n is 1,2 or 3) or a lower acyl group, such as formyl or acetyl. Preferred values of $R_4(CH_2)_n-$ are methyl, β-hydroxyethyl, allyl, formyl, phenyl, and benzyl.

The present invention also concerns in addition salts thereof with non-toxic acids, pharmaceutically acceptable, such as hydrochlorides, maleates, methanesulphonates and such like.

The present invention concerns in particular: -6-chloro derivatives of the formula:

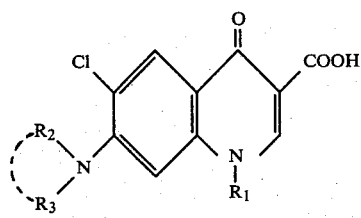

in which $R_1$, $R_2$ and $R_3$ are as defined above, -6-fluoro derivatives of the formula:

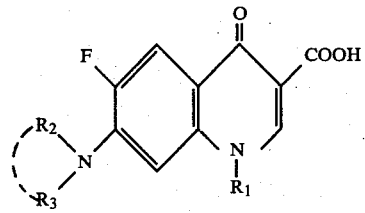

in which $R_1$, $R_2$, $R_3$ are as defined above, -1-vinyl derivatives of the formula:

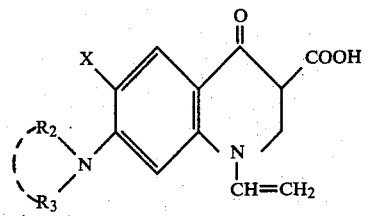

in which X, $R_2$, $R_3$ are as defined above, -7-morpholino derivatives of the formula:

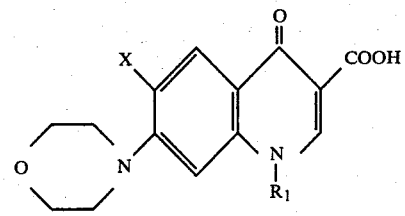

in which X and $R_1$ are as defined above.

The most interesting compounds include the following:

6-chloro derivatives of the formula:

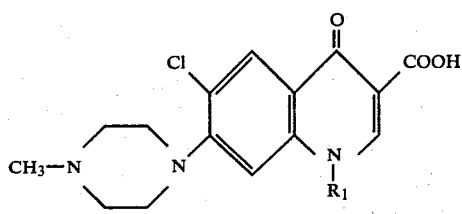

in which $R_1$ is a methyl, ethyl, vinyl or allyl radical, -6-fluoro derivatives of the formula:

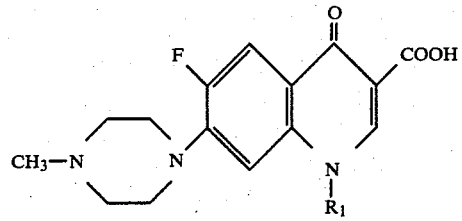

in which $R_1$ is a methyl, ethyl, vinyl or allyl radical, -6-fluoro derivatives of the formula:

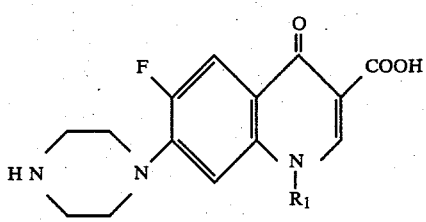

in which $R_1$ is a methyl, ethyl, vinyl or allyl radical.

The present invention also comprises a process for the preparation of the compounds claimed, which comprises condensing a secondary amine of the formula (II)

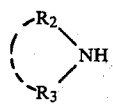 II in which $R_2$ and $R_3$ have the above-stated meanings, with a 1-substituted-6-halogeno-7-chloro-4-oxo-1,4-dihydro-quinoline-3-carboxylic acid of the formula (III):

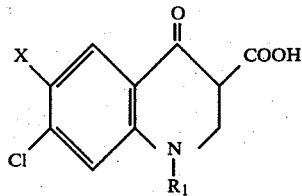 III in which $R_1$ and X have the above-stated meaning.

The substitution reaction is selective and occurs only at the chlorine atome in the 7-position. Thus, when X is Cl, if the product of the reaction is subjected to catalytic hydrogenation in an alkaline medium in the presence of palladium on charcoal, the corresponding 1-substituted-7-disubstituted-amino-4-oxo-1,4-dihydro-quinoline-3-carboxylic acid is obtained as the exclusive product.

The reaction of the dihalogeno-acid III with the amine II is preferably carried out by heating the two reactants in substantially equimolar proportions in the presence of an acceptor for the hydracid which is formed in the reaction.

The acid acceptors may be either an inorganic acceptor, such as an alkali metal carbonate, or, preferably, an organic acceptor, such as a tertiary alkylamine, for example triethylamine or tributylamine. In the latter case, a slight excess (1.1 to 1.5 mols) of secondary amine and a considerable excess (2 to 10 molecules) of the tertiary amine are used per mole of the dihalogeno-acid III.

The hydracid acceptor may also be an excess of the secondary base used in the reaction; for example 2 to 10 mols of secondary amine $R_2R_3NH$ can be used per mol of the dihalogeno-acid III.

As the chlorine atom in the 7-position of the dihalogeno-acid III is relatively unreactive, it is desirable to carry out the reaction at a temperature of from 100° to 200° C., more preferably from 110° to 150° C., in order to obtain sufficiently fast reaction rates.

In order to follow the reaction, it is desirable to carry out the reaction in a solvent which is such that the mixture remains homogeneous after dissolution of the dihalogeno-acid III. Sampling of the reaction mixture then enables the amount of ionised chloride formed to be determined and thus the course of the reaction. For this purpose, solvents with a boiling point of at least 100° C. are preferably used. Suitable solvents are, for example, aliphatic alcohols, glycol, glycol ethers (such as methyl cellosolve), dimethylformamide, dimethylacetamide and dimethylsulphoxide.

When the secondary amine used is piperazine, with the object of obtaining a monosubstituted piperazine derivative ($R_4$=H,n=0 in the above partial formula), it is necessary, when using the above-mentioned solvents, to use a large excess of piperazine (6 to 10 mols per mol of dihalogeno-acid). Despite this precaution, more or less significant amounts of the N,N'-disubstituted piperazine derivative are always formed, which reduces the yield of the desired monosubstituted derivative and renders its isolation and purification more difficult.

We have found that the selectivity of the reaction can be very substantially improved in this case by the use of pyridine or a methylated derivative thereof (picoline, lutidine or collidine) as the solvent. The preferred use of pyridine or such a derivative enables the formation of N,N'-disubstituted piperazine derivatives to be very substantially reduced and also avoid the necessity for using a large excess of piperazine. Using pyridine or a methyl derivative thereof as the solvent and under the temperature conditions mentioned above, the use of from 2 to 5 mols of piperazine per mol of dihalogeno-acid III enables the reaction to be completed in 4 to 10 hours.

This same solvent, i.e. pyridine or methyl derivative, can, of course, also be used for reactions with secondary amines other than piperazine.

Mixtures of two or more of the solvents mentioned above can also be used.

In the case where the amine used has a boiling point which is lower than the temperature necessary for the reaction, the latter should be carried out in an autoclave.

The amount of solvent (or solvent mixture) used are such that the concentration of the reactants therein is from 10 to 30%.

For reaction temperatures of from 110° to 150° C., the reaction time depends on the reactivity of the base; for any given case, at least 90% of the halogen is removed in the ionised form in reaction times of from 2 to 20 hours.

The isolation of the reaction product depends on its own physico-chemical characteristics and on those of the solvent (or solvents) used. According to these factors, the following situations can arise:

(a) following dissolution of the reactants in the solvent, the reaction product precipitates during the course of the reaction;

(b) the reaction product crystallises from the mixture after the cooling of the latter to room temperature.

In both these cases, the reaction mixture is cooled, diluted, if appropriate, with water or a lower alcohol, and the solid product is filtered off.

(c) the product remains in solution after cooling.

In this case, the reaction mixture is concentrated to dryness. The residue is taken up in water, which usually leads to partial precipitation of the product. The strongly alkaline mixture is brought to pH 7–7.5 by the addition of an inorganic or organic acid, and the precipitate is filtered off.

In a variant of this procedure, the reaction product, after the mixture has been concentrated and the residue taken up in water, is totally dissolved by the addition of an alkali metal hydroxide solution. The solution thus obtained sometimes exhibits slight turbidity which is caused by the presence of non-acidic substances; these substances are then removed by filtration, optionally in the presence of animal charcoal, or by extraction with an appropriate solvent. The alkaline solution is brought to pH 7–7.5, and the reaction product is isolated as indicated previously.

After neutralisation, the solid can optionally be extracted with a suitable solvent. After concentration of the extract, the crude product is then obtained, which is purified by recrystallisation from an appropriate solvent, as in the preceding cases.

When $R_1$ in formula I is a vinyl group, the compounds according to the invention can be prepared by either of two processes depending on whether the vinyl substituent in the 1-position is introduced at the beginning of the synthesis process (process A) or at the end of the process (process B). The reaction schemes below show the stages of these two processes for the case where X in formula I is fluorine. The two methods use 7-chloro-3-ethoxycarbonyl-6-fluoro-1-(2-hydroxyethyl)-4-oxo-1,4-dihydro-quinoline (V) as an intermediate. The intermediate V is obtained by the alkylation of 7-chloro-3-ethoxycarbonyl-6-fluoro-4-oxo-1,4-dihydroquinoline (IV) with a 2-halogeno-ethanol $XCH_2—CH_2OH$, in which X is a halogen atom, in the presence of a base, for example a neutral alkali metal carbonate. The reaction is suitably carried out at a temperature of from 100° to 120° C., preferably in dimethylformamide (DMF). For each mole of the ester IV, in solution in 5 to 10 times its weight of DMF, an excess of alkali metal carbonate (2 to 3 moles) and an excess of halogeno-ethanol (4 moles) are preferably used. The reaction is complete when the pH of the reaction medium becomes neutral, which, when using bromoethanol, is generally obtained after 4 hours of heating. When chloroethanol is used as the alkylation agent, it is preferred to carry out the reaction in the presence of an alkali metal bromide, such as potassium bromide, in order to increase the reaction rate, the bromide suitably being used in a proportion of 0.1 to 1.0 mole per mole of chloroethanol. After concentration under reduced pressure and dilution with water, the ester V, m.p. 202° C., precipitates; it is then dried and recrystallised, from a suitable solvent.

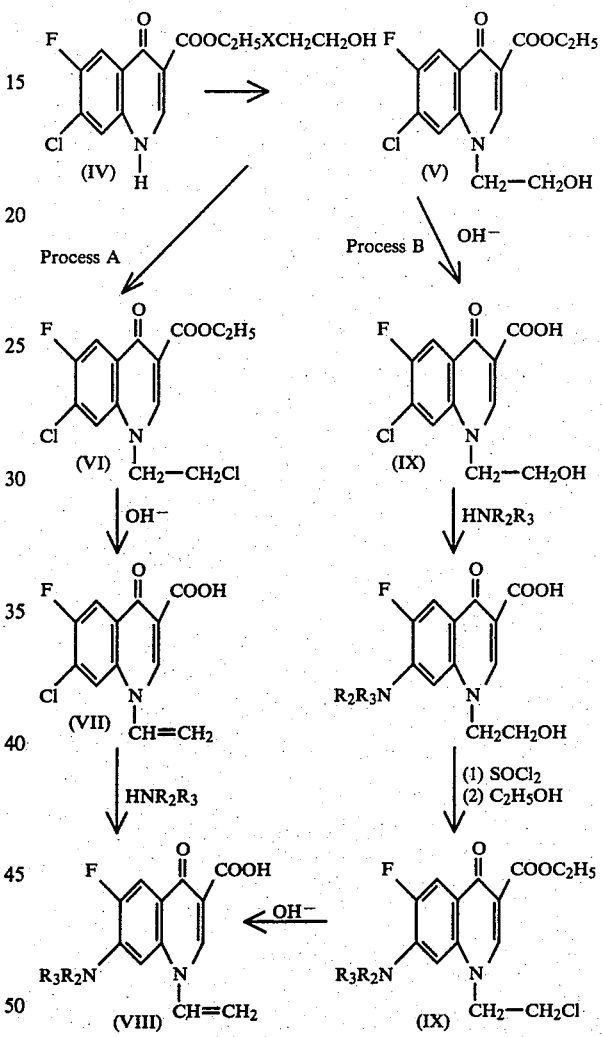

In Process A, the ester V is halogenated by any suitable known process, preferably with thionyl chloride, to form 7-chloro-1-(2-chloroethyl)-3-ethoxycarbonyl-6-fluoro-4-oxo-1,4-dihydro-quinoline (VI), m.p. 222° C. The latter, heated with an excess of alkali metal hydroxide in aqueous alcoholic solution gives, after acidification, 7-chloro-6-fluoro-4-oxo-1-vinyl-1,4-dihydro-quinoline-3-carboxylic acid (VII), m.p. 210° C. On heating the latter, under the conditions previously described, with a secondary amine $HNR_2R_3$, a compound according to the invention (VIII) in which the substituent $R_1$ is a vinyl group, is obtained. The product is isolated and purified by the methods described above.

Contrary to what has previously been described for compounds of formula I in which $R_1$ is a lower alkyl group, the conversion of compound VII to compound VIII is, in the case of Process A, more complex. The quantity of chloride ions formed, whatever the reaction conditions, seldom exceeds 60% of theory and the reaction products VIII are only obtained in relatively low yields.

In Process B, the ester V is saponified with an alkali metal hydroxide and the mixture is acidified to give 7-chloro-6-fluoro-1-(2-hydroxyethyl)-4-oxo-1,4-dihydro-quinoline-3-carboxylic acid (IX), m.p. 266° C. The latter is treated with an excess of a secondary amine $HNR_2R_3$, under the conditions previously described, to give 7-dialkylamino-6-fluoro-1-(2-hydroxyethyl)-4-oxo-1,4-dihydro-quinoline-3-carboxylic acid (X). The latter is chlorinated with thionyl chloride, preferably at reflux temperature for 2 to 4 hours, to give, after evaporation of the excess reactant and taking up the residue in ethanol, 7-dialkylamino-3-ethoxycarbonyl-1-(2-chloroethyl)-6-fluoro-4-oxo-1,4-dihydro-quinoline (XI). Saponification of the ester XI with an aqueous alcoholic solution of an alkali metal hydroxide gives, after neutralisation, a compound according to the invention, VIII, in which $R_1$ is a vinyl group.

Process B is generally preferred over Process A and the latter is, in practice, only used when the $R_2R_3N$-radical contains functions which are sensitive to the thionyl chloride used in the stage X to XI of process B.

In order that the invention may be more fully understood, the following examples are given by way of illustration. The melting points indicated were determined on a Kofler block for temperatures up to 260° C., and on a Maquenne block for temperature above 260° C. Except were specifically indicated, the analyses mentioned were carried out on the products after drying at 150° C. in vacuo (5 mm Hg).

EXAMPLE 1

6-Chloro-1-ethyl-7-(4-methylpiperazinyl)-4-oxo-1,4-dihydro-quinoline-3-carboxylic acid A solution of 4.3 g of 6,7-dichloro-1-ethyl-4-oxo-1,4-dihydro-quinoline-3-carboxylic acid and 9 g of 1-methylpiperazine in 45 cm³ of dimethylsulphoxide was stirred and heated to 110° C. Determination of the Cl ions in the mixture showed that 80% of the theoretical amount of halogen (for the removal of one Cl atom) was in the ionised form after 4 hours of heating. The heating and stirring were continued for a further 3 hours. The reaction product crystallised on cooling. It was filtered off, washed with ethanol and recrystallised from 40 cm³ of methylcellosolve.

2.7 g of 6-chloro-1-ethyl-7-(4-methylpiperazinyl)-4-oxo-1,4-dihydro-quinoline-3-carboxylic acid were obtained; m.p.=260° C.

Analysis for $C_{17}H_{20}ClN_3O_3$ (molecular weight 349.8): Calculated % C 58.36, H 5.76, N 12.01, Cl 10.13; Found % C 58.12, H 5.70, N 12.00, Cl 10.48.

Identification 1.75 g of this acid were dissolved in 30 cm³ of 70% aqueous ethanol in the presence of 5 cm³ of N sodium hydroxide and 1.4 cm³ of triethylamine were added. The solution thus obtained was stirred in a hydrogen atmosphere at atmospheric pressure and room temperature (23° C.) in the presence of 0.8 g of 5% palladium-on-charcoal which had been previously saturated in the presence of 5 cm³ of ethanol. Absorption (135 cm³; theoretical volume for 1 mol: 121 cm³) ceased after 2 hours 30 minutes. The solution was filtered and concentrated to dryness in vacuo. The residue was dissolved in 20 cm³ of water and mixed with 0.3 cm³ of acetic acid. The precipitate (hydrochloride) was recrystallised from 100 cm³ of a saturated aqueous solution of sodium acetate. The solid was filtered off and recrystallised from methyl cellosolve. 0.65 g of 1-ethyl-7-(4-methylpiperazinyl)-4-oxo-1,4-dihydro-quinoline-3-carboxylic acid, m.p. 215° C., were obtained, which was identical (melting point and infrared spectrum) to the product obtained by the condensation of 1-methylpiperazine with 7-chloro-1-ethyl-4-oxo-1,4-dihydro-quinoline-3-carboxylic acid.

EXAMPLE 2

A solution of 4.3 g (0.015 mol) of 6,7-dichloro-1-ethyl-4-oxo-1,4-dihydro-quinoline-3-carboxylic acid and 9 g of 1-methylpiperazine in a mixture of methyl cellosolve (45 cm³) and dimethylformamide (10 cm³) was heated to reflux temperature. After 6 hours, 75% of the theoretical amount of ionized chlorine (1 atom) had been released into the mixture. Heating was continued for a further 2 hours. The solution was concentrated to dryness in vacuo. The residue was taken up in 20 cm³ of ethanol. The solid, which was filtered off and recrystallised from methyl cellosolve, gave 2.78 g of 6-chloro-1-ethyl-7-(4-methylpiperazinyl)-4-oxo-1,4-dihydro-quinoline-3-carboxylic acid, m.p. 260° C., which was identical to the compound described in Example 1.

EXAMPLE 3

6-Chloro-1-ethyl-4-oxo-7-piperazinyl-1,4-dihydro-quinoline-3-carboxylic acid 2.86 g of 6,7-dichloro-1-ethyl-4-oxo-1,4-dihydro-quinoline-3-carboxylic acid and 10 g of piperazine in 30 cm³ of dimethylsulphoxide were stirred and heated to 110° C. After two hours, the reaction was complete. After evaporation of the solvent under a good vacuum, the residue was taken up in 20 cm³ of water. The solid which precipitated was filtered off and recrystallised from 50 cm³ of a mixture of ethanol (1 volume) and methyl cellosolve (1 volume), which enabled an insoluble impurity, which was separated off by filtration of the hot solution to be removed. The crystals, which precipitated on cooling, were filtered off and recrystallised from the same solvent mixture. 1.2 g of 6-chloro-1-ethyl-4-oxo-7-piperazinyl-1,4-dihydro-quinoline-3-carboxylic acid were obtained; m.p. 228°–232° C.

Analysis for $C_{16}H_{18}ClN_3O_3$ (molecular weight 335.8): Calculated % C 57.22, H 5.40, N 12.51, Cl 10.56; Found % C 56.99, H 5.57, N 12.64, Cl 10.79.

This product was hygroscopic. In a moist atmosphere, it absorbed water and gave a dihydrate which lost its water of crystallisation between 100° and 150° C., and then melted at 228°–230° C. (anhydrous product).

Analysis for $C_{16}H_{18}ClN_3O_3.2\ H_2O$ (molecular weight 371.8): Calculated % C 51.68, H 5.96, N 11.30; Found % C 51.48, H 5.71, N 11.11.

EXAMPLE 4

6-Chloro-1-ethyl-7-[4-(β-hydroxyethyl)-piperazinyl]-4-oxo-1,4-dihydro-quinoline-3-carboxylic acid As described in Example 1, 4.3 g of 6,7-dichloro-1-ethyl-4-oxo-1,4-dihydro-3-quinoline-carboxylic acid and 10.6 g of 1-(β-hydroxyethyl)-piperazine in 45 cm³ of DMSO (dimethylsulphoxide) were heated for 3 hours at 110° C. After evaporation of the solvent under a good vacuum, the viscous residue was taken up in 20 cm³ of isopropanol; the mixture was stirred and heated under reflux for 20 minutes. After standing for one night at 4° C., the solid was filtered off, washed with ethanol and recrystallised from methyl cellosolve (15 cm³). 3.5 g of 6-chloro-1-ethyl-7-[4-(β-hydroxyethyl)-piperazinyl]-4-oxo-1,4-dihydro-quinoline-3-carboxylic acid, m.p. 215° C., were obtained.

Analysis for $C_{18}H_{22}ClN_3O_4$ (molecular weight 379.5): Calculated % C 59.61, H 5.84, N 11.06, Cl 9.33; Found % C 57.18, H 5.91, N 11.27, Cl 9.18.

EXAMPLE 5

7-(4-Benzylpiperazinyl)-6-chloro-1-ethyl-4-oxo-1,4-dihydro-quinoline-3-carboxylic acid A solution of 4.3 g of 6,7-dichloro-1-ethyl-4-oxo-1,4-dihydro-quinoline-3-carboxylic acid and 10.5 g of 1-benzylpiperazine in 45 cm³ of DMSO was stirred and heated to 110° C. After 2 hours, the amount of Cl⁻ ions in the reaction mixture corresponded to 94% of the amount calculated for the removal of one halogen atom. After evaporation of the solvent, the reaction product was isolated as in the preceding example; it was purified by recrystallisation from methyl cellosolve. 3.2 g of 7-(4-benzylpiperazinyl)-6-chloro-1-ethyl-4-oxo-1,4-dihydro-quinoline-3-carboxylic acid, m.p. 228° C., were obtained.

Analysis for $C_{23}H_{24}ClN_3O_3$ (molecular weight 425.9): Calculated % C 64.85, H 5.68, N 9.86, Cl 8.32; Found % C 64.73, H 5.82, N 9.67, Cl 8.39.

EXAMPLE 6

6-Chloro-1-ethyl-7-(4-formylpiperazinyl)-4-oxo-1,4-dihydro-3-quinoline carboxylic acid 4.3 g of 6,7-dichloro-1-ethyl-4-oxo-1,4-dihydro-quinoline-3-carboxylic acid, 10 g of 1-formylpiperazine and 45 cm³ of DMSO were heated for 3 hours at 110°-120° C. The reaction product was isolated and purified as in the preceding example. 2 g of 6-chloro-1-ethyl-7-(4-formyl-piperazinyl)-4-oxo-1,4-dihydro-quinoline-3-carboxylic acid, which melted with decomposition at about 300° C., were obtained.

Analysis for $C_{17}H_{18}ClN_3O_4$ (molecular weight 363.79): Calculated % C 56.12, H 4.98, N 11.55, Cl 9.74; Found % C 56.13, H 5.19, N 11.42, Cl 9.70.

EXAMPLE 7

6-Chloro-1-ethyl-7-morpholino-4-oxo-1,4-dihydro-quinoline-3-carboxylic acid 6,7-Dichloro-1-ethyl-4-oxo-1,4-dihydro-quinoline-3-carboxylic acid (4.3 g) and morpholine (10 cm³) in DMSO (45 cm³) were heated for 3 hours at 110° C. under the same conditions as in Example 6. The reaction product crystallised on cooling. It was filtered off and recrystallised from 40 cm³ of a mixture of DMF (dimethylformamide; 1 volume) and methyl cellosolve (1 volume). 3.3 g of 6-chloro-1-ethyl-7-morpholino-4-oxo-1,4-dihydro-quinoline-3-carboxylic acid, m.p. 266° C., were obtained.

Analysis for $C_{16}H_{17}ClN_2O_4$ (molecular weight 336.8): Calculated % C 57.05, H 5.08, N 8.32, Cl 10.52; Found % C 56.82, H 5.31, N 8.39, Cl 10.74.

EXAMPLE 8

6-Chloro-1-ethyl-4-oxo-7-piperidino-1,4-dihydro-quinoline-3-carboxylic acid

A solution of 4.3 g of 6,7-dichloro-1-ethyl-4-oxo-1,4-dihydro-quinoline-3-carboxylic acid and 5.5 cm³ of piperidine in a mixture of 20 cm³ of DMF and 20 cm³ of methyl cellosolve was heated for 5 hours at 110° C. After concentration of the solution in vacuo, the residue was taken up in 50 cm³ of isopropanol. The solid was filtered off and recrystallised from methyl cellosolve (50 cm³). 2.4 g of 6-chloro-1-ethyl-4-oxo-7-piperidino-1,4-dihydro-quinoline-3-carboxylic acid, m.p. 230° C., were obtained.

Analysis for $C_{17}H_{19}ClN_2O_3$ (molecular weight 334.8): Calculated % C 60.98, H 5.72, N 8.37, Cl 10.59; Found % C. 60.97, H 5.81, N 8.21, Cl 10.79.

EXAMPLE 9

6-Chloro-1-ethyl-4-oxo-7-pyrrolidino-1,4-dihydro-quinoline-3-carboxylic acid

A mixture of 6,7-dichloro-1-ethyl-4-oxo-1,4-dihydro-quinoline-3-carboxylic acid (4.3 g), pyrrolidine (10 cm³) and DMSO (45 cm³) was heated for 2 hours at 110° C. Part of the reaction product precipitated during the reaction. After cooling, it was filtered off and recrystallised from DMF (50 cm³). 3 g of 6-chloro-1-ethyl-4-oxo-7-pyrrolidino-1,4-dihydro-quinoline-3-carboxylic acid, m.p. 325° C., were obtained.

Analysis for $C_{16}H_{17}ClN_2O_3$ (molecular weight 320.8): Calculated % C 59.90, H 5.34, N 8.73, Cl 11.05; Found % C 59.93, H 5.43, N 8.70, Cl 10.90.

EXAMPLE 10

6-Chloro-7-dimethylamino-1-ethyl-4-oxo 1,4-dihydro-quinoline-3-carboxylic acid 13 g of dimethylamine were dissolved in a mixture of DMF (20 cm³) and methyl cellosolve (20 cm³). 4.3 g of 6,7-dichloro-1-ethyl-4-oxo-1,4-dihydro-quinoline-3-carboxylic acid were added and the mixture was heated, whilst stirring, in an autoclave at 120°-130° C. for 7 hours. After cooling, the solution was concentrated to dryness in vacuo and the residue was taken up in 20 cm³ of water. The solid was filtered off and recrystallised from methyl cellosolve (30 cm³). 3.9 g of 6-chloro-7-dimethylamino-1-ethyl-4-oxo-1,4-dihydro-quinoline-3-carboxylic acid, m.p. 210° C., were obtained.

Analysis for $C_{14}H_{15}ClN_2O_3$ (molecular weight 294.7): Calculated % C 57.05, H 5.13, N 9.51, Cl 12.03; Found % C 57.60, H 5.14, N 9.22, Cl 11.82.

EXAMPLE 11

7-(4-Allylpiperazinyl)-6-chloro-1-ethyl-4-oxo-1,4-dihydro-quinoline-3-carboxylic acid 2 g of 6,7-dichloro-1-ethyl-4-oxo-1,4-dihydro quinoline-3-carboxylic acid, 3.8 g of 1-allylpiperazine and 20 cm³ of pyridine were heated under reflux. After 2 hours, dissolution of the acid was complete; after 11 hours, determination of the ionised chlorine (93% of theory) showed that the reaction was substantially complete. The solution was concentrated to dryness in vacuo, the residue was taken up in water (20 cm³) and the suspension was brought to pH 7.5 by the addition of acetic acid, whilst stirring. The precipitate was filtered off, washed with water and recrystallised from methyl cellosolve. 2.05 g of 7-(4-allylpiperazinyl)-6-chloro-1- ethyl-4-oxo-1,4-dihydro-quinoline-3-carboxylic acid, m.p. 212° C., were obtained.

Analysis for $C_{19}H_{22}ClN_3O_3$ (molecular weight 375.85): Calculated % C 60.71, H 5.90, N 11.18, Cl 9.43; Found % C 60.47, H 5.99, N 11.07, Cl 9.29.

EXAMPLE 12

6-Chloro-1-ethyl-4-oxo-7-(4-phenylpiperazinyl)-1,4-dihydro-quinoline-3-carboxylic acid 2.15 g of 6,7-dichloro-1-ethyl-4-oxo-1,4-dihydro-quinoline-3-carboxylic acid, 6.5 g of 1-phenylpiperazine and 20 cm³ of pyridine were heated under reflux for 16 hours. The solvent was removed in vacuo and the residue was taken up in 20 cm³ of water. The suspension obtained was stirred and brought to pH 7 by the addition of acetic acid. The solid was filtered off and recrystallised from methyl cellosolve. 1.7 g of 6-chloro-1-ethyl-4-oxo-7-(4-phenylpiperazinyl)-1,4-dihydro-quinoline-3-carboxylic acid, m.p. 234°-235° C., were obtained.

Analysis for $C_{22}H_{22}ClN_3O_3$ (molecular weight=441.88): Calculated % C 64.15, H 5.38, N 10.20, Cl 8.61; Found % C 63.81, H 5.75, N 9.95, CCl 8.74.

EXAMPLE 13

17.2 g of 6,7-dichloro-1-ethyl-4-oxo-1,4-dihydro-quinoline-3-carboxylic acid, 160 cm³ of pyridine and 26 cm³ of 1-methylpiperazine were heated under reflux whilst stirring. After 14 hours, the ionised chlorine content of the reaction mixture corresponded to 94% of theory.

The solvent was evaporated off in vacuo, the residue was taken up in 300 cm³ of water, the suspension was stirred, and a solution of acetic acid, which had been diluted to ½ strength, was added to the suspension until the pH of the mixture was between 7.5 and 8. The mixture was allowed to stand overnight at 4° C. The solid was filtered off, washed with water and then alcohol, and recrystallised from 200 cm³ of methyl cellosolve. 17.2 g of 6-chloro-1-ethyl-7-(4-methylpiperazinyl)-4-oxo-1,4-dihydro-quinoline-3-carboxylic acid, m.p. 260° C., were obtained, which was identical to the product described in Example 1.

EXAMPLE 14

14.3 g of 6,7-dichloro-1-ethyl-4-oxo-1,4-dihydro-quinoline-3-carboxylic acid, 17.2 of anhydrous piperazine and 150 cm³ of pyridine were heated under reflux for 6 hours, whilst stirring. After the first quarter of an hour, the solution was homogeneous and then, after about 1 hour 30 minutes, the formation of a precipitate (the hydrochloride of the reaction product) was observed.

After cooling, the mixture was diluted with 80 cm³ of water and the solution was concentrated to dryness in vacuo; the residue was taken up in 100 cm³ of water. The suspension obtained was stirred and brought to pH 7.5 as indicated in the preceding example. The precipitate was filtered off, washed with water and then recrystallised from a mixture of methyl cellosolve (1 volume) and ethanol (1 volume). 15 g of 6-chloro-1-ethyl-4-oxo-7-piperazinyl-1,4-dihydro-quinoline-3-carboxylic acid, m.p. 228°-232° C., were obtained, which was identical to the product of Example 3.

EXAMPLE 15

6-Chloro-1-methyl-7-(4-methylpiperazinyl)-4-oxo-1,4-dihydro-quinoline-3-carboxylic acid 2.18 g of 6,7-dichloro-1-methyl-4-oxo-1,4-dihydro-quinoline-3-carboxylic acid, 3.5 cm³ of 1-methylpiperazine and 25 cm³ of dimethylsulphoxide were heated at 110° C. for 3 hours. The solvent was evaporated off in vacuo and the residue was taken up in 100 cm³ of water. The suspension was stirred and mixed with 20 cm³ of N sodium hydroxide solution. The solution obtained, which was slightly turbid, was stirred with animal charcoal and filtered, and then brought to pH 7.5 by the addition of acetic acid. The precipitate was filtered off, washed with water and then recrystallised from methyl cellosolve. 1 g of 6-chloro-1-methyl-7-(4-methylpiperazinyl)-4-oxo-1,4-dihydro-quinoline-3-carboxylic acid, m.p. 286° C., were obtained.

Analysis: for $C_{16}H_{18}ClN_3O_3$ (molecular weight 335.78): Calculated % C 57.22, H 5.40, N 12.51; Found % C 57.51, H 5.98, N 12.65.

EXAMPLE 16

6-Chloro-1-methyl-7-morpholino-4-oxo-1,4-dihydro-quinoline-3-carboxylic acid 2.18 g of 6,7-dichloro-1-methyl-4-oxo-1,4-dihydro-quinoline-3-carboxylic acid, 3 cm³ of morpholine and 30 cm³ of DMSO were heated for 5 hours at 125°-130° C. About 3 hours were required for total dissolution of the dihalogeno-acid, and the reaction product then precipitated from the mixture. After returning to room temperature, the mixture was diluted with 30 cm³ of water. The precipitate was filtered off, washed with water and recrystallised from a mixture of DMF (1 volume) and methylcellosolve (1 volume). 1.68 g of 6-chloro-1-methyl-7-morpholino-4-oxo-1,4-dihydro quinoline-3-carboxylic acid were obtained; m.p. 334° C.

Analysis for $C_{15}H_{15}ClN_2O_4$ (molecular weight 322.74): Calculated % C 55.82, H 4.68, N 8.68; Found % C 55.72, H 4.65, N 8.35.

EXAMPLE 17

6-Chloro-1-methyl-4-oxo-7-piperazinyl-1,4-dihydro-quinoline-3-carboxylic acid 2.45 g of 6,7-dichloro-1-methyl-4-oxo-1,4-dihydro-quinoline-3-carboxylic acid, 3.1 g of piperazine and 30 cm³ of pyridine were heated under reflux for 8 hours. The dihalogeno-acid went rapidly into solution; after 5 hours, a precipitate appeared which consisted principally of the hydrochloride of the reaction product. The solvent was evaporated off, the residue was taken up in 100 cm³ of water, and 20 cm³ of N sodium hyxroxide solution were then added to the mixture. The solution, which was slightly turbid, was brought to pH 7.5, by the addition of acetic acid. The precipitate was filtered off and suspended in 100 cm³ of water; the addition of 10 cm³ of N HCl led to almost total dissolution. A slight amount of insoluble material was removed by filtration. The solution was brought to pH 7.5 by the addition of N NaOH. The solid was filtered off and recrystallised from a mixture of DMF (1 volume) and methyl cellosolve (2 volumes). 1.32 g of 6-chloro-1-methyl-4-oxo-7-piperazinyl-1,4-dihydro-quinoline-3-carboxylic acid, m.p. 288° C., were obtained.

Analysis for $C_{15}H_{16}ClN_3O_3$ (molecular weight 321.76): Calculated % C 55.98, H 5.01, N 13.06; Found % C 56.04, H 5.22, N 12.80.

EXAMPLE 18

6-Bromo-1-ethyl-7-(4-methylpiperazinyl)-4-oxo-1,4-dihydro-quinoline-3-carboxylic acid (a) 3.3 g of 6-bromo-7-chloro-1-ethyl-4-oxo-1,4-dihydro-quinoline-3-carboxylic acid (0.01 mol) and 4.5 cm³ of 1-methylpiperazine (0.04 mol) in solution in 30 cm³ of dimethylsulphoxide, were heated at 110° C. for 4 hours. After cooling, the solution was diluted with 250 cm³ of water. The precipitate formed was filtered off, washed with water and recrystallised from 50 cm³ of methyl cellosolve. 1.3 g of 6-bromo-1-ethyl-7-(4-methylpiperazinyl)-4-oxo-1,4-dihydro-quinoline-3-carboxylic acid, m.p. 209C (decomposition), were obtained.

Analysis for $C_{17}H_{20}BrN_2O_3$ (molecular weight=394.26): Calculated % C 51.78, H 5.11, N 10.65, Br 20.26; Found % C 51.72, H 5.36, N 10.56, Br 20.24.

6-Bromo-7-chloro-1-ethyl-4-oxo-1,4-dihydro-quinoline-3-carboxylic acid was prepared from 3-chloro-4-bromoaniline by a known process as follows: 23 g of 3-chloro-4-bromoaniline and 23 g of ethyl ethoxymethyl-enemalonate were heated at 100° C. in a round-bottomed flask equipped with a descending condenser which enabled the alcohol formed in the reaction to be collected. The reaction ended after heating for 2 hours. After cooling, the solid was recrystallised from cyclohexane. 33 g (yield 88%) of ethyl 3-chloro-4-bromoanilinomethylenemalonate, m.p. 86°–87° C., were obtained.

33 g of the above compound were added to 50 cm³ of Dowtherm, heated at 250° C. and stirred in a round-bottomed flask equipped with a descending condenser which enabled the alcohol formed in the reaction to be collected; the reaction was complete after heating for 15 minutes. After cooling, the contents of the round-bottomed flask were taken up in 200 m³ of ethyl acetate. The solid was separated and recrystallised from dimethylformamide. 27.9 g of 6-bromo-7-chloro-3-ethoxycarbonyl-4-hydroxy-quinoline, m.p. 368°–370° C. (decomposition), were obtained. 13 g of 6-bromo-7-chloro-3-ethoxycarbonyl-4-hydroxyquinoline, 11 g of potassium carbonate and 100 cm³ of dimethylformamide were heated at 110° C. for 1 hour, whilst stirring. After cooling to 80° C., 16 cm³ of ethyl iodide were added to the mixture which was stirred and heated at 110° C. for 4 hours. After concentration to dryness in vacuo, the residue was taken up in 200 cm³ of water. The mixture was extracted with chloroform (3×100 cm³), and the combined organic extracts were washed with water, dried (MgSO₄) and concentrated to dryness. The residue, recrystallised from 95 cm³ of isopropanol, gave 10 g of 6-bromo-7-chloro-1-ethyl-4-oxo-1,4-dihydro-3-ethoxycarbonylquinoline, m.p. 166° C. 10 g of the above ester were added to an aqueous-alcoholic solution of sodium hydroxide (NaOH:2.25 g, water:50 cm³, ethanol:100 cm³). The mixture was heated under reflux for 30 minutes. The solution was concentrated to dryness in vacuo. The residue was suspended in 100 cm³ of water. The solution was acidified by adding 3.4 cm³ of acetic acid. The solid was separated and recrystallised from DMF (90 cm³). 8.1 g (89%) of 6-bromo-7-chloro-1-ethyl-4-oxo-1,4-dihydro-quinoline-3-carboxylic acid, m.p. 320° C. (decomposition), were obtained.

EXAMPLE 19

6-Bromo-1-ethyl-7-morpholino-4-oxo-1,4-dihydro-quinoline-3-carboxylic acid 3.3 g of 6-bromo-7-chloro-1-ethyl-4-oxo-1,4-dihydro-quinoline-3-carboxylic acid and 3.5 g of morpholine, in solution in 30 cm³ of DMSO, were heated at 110° C. for 6 hours.

After cooling, the mixture was diluted with 200 cm³ of water. The precipitate was filtered off, washed with water and recrystallised from methylcellosolve (50 cm³). 2.4 g (yield 63%) of 6-bromo-1-ethyl-7-morpholino-4-oxo-1,4-dihydro-quinoline-3-carboxylic acid, m.p. 266° C., were obtained.

Analysis for $C_{16}H_{17}BrN_2O_4$ (molecular weight 380.5): Calculated % C 50.50, H 4.50, N 7.36; Found % C 50.38, H 4.68, N 7.09.

EXAMPLE 20

1-Ethyl-6-fluoro-7-(4-methylpiperazinyl)-4-oxo-1,4-dihydro-quinoline-3-carboxylic acid 113 g (0.42 mol) of 7-chloro-6-fluoro-1-ethyl-4-oxo-1,4-dihydro-quinoline-3-carboxylic acid, 170 g (1.68 mol) of 1-methylpiperazine and 600 cm³ of DMSO were stirred and heated at 100° C. for 7 hours 30 minutes.

The solvent was removed by distillation in vacuo. The residue was taken up in 1,300 cm³ of 10% aqueous acetic acid. The mixture was stirred and heated at 60° C. The solution, which was slightly turbid, was treated with 10 g of animal charcoal and stirred at the same temperature for half an hour. After filtration and cooling, the solution was brought to pH 7.5 by the addition of 5 N NaOH, whilst stirring vigorously. After standing for one night at 4° C., the precipitate was filtered off, washed with water and dried. The crude product (85 g) was recrystallised from 500 cm³ of DMF. 80 g of 1-ethyl-6-fluoro-7-(4-methylpiperazinyl)-4-oxo-1,4-dihydro-quinoline-3-carboxylic acid, m.p. 270°–272° C. (decomposition, were obtained.

Analysis for $C_{17}H_{20}FN_3O_3$ (molecular weight 333.35): Calculated % C 61.26, H 6.00, N 12.61; Found % C 60.94, H 5.93, N 12.75.

7-Chloro-6-fluoro-1-ethyl-4-oxo-1,4-dihydroquinoline-3-carboxylic acid, used as the starting material, was prepared as follows:

165 g of 3-chloro-4-fluoroaniline and 254 g of ethyl ethoxymethylenemalonate were stirred and heated at 130° C. The alcohol formed during the reaction was collected by distillation. The reaction was complete after 1 hour 30 minutes. The reaction product, m.p. 68°–69° C., crystallised on cooling. 119 g of ethyl 3-chloro-4-fluoroanilinomethylenemalonate, in solution at 100° C. in 200 cm³ of Dowtherm, were added to 200 cm³ of the same solvent, stirred vigorously and heated at 250° C. in a round-bottomed flask equipped with a descending condenser. After the addition, this temperature and the stirring were maintained until the alcohol formed in the reaction had finished distilling, which required about 45 minutes. After cooling, the precipitate formed was filtered off, washed with acetone and dried in air, and 91 g of 7-chloro-3-ethoxycarbonyl-6-fluoro-4-hydroxyquinoline, m.p. 335° C. (decomposition), were obtained. 80.85 g of the above ester, 500 cm³ of dimethylformamide and 82.8 g of potassium carbonate were heated at 110° C. for one hour, whilst stirring, in a round-bottomed flask equipped with a reflux condenser. During this time, the starting material dissolved. After cooling to 60° C., 187 g of ethyl iodide were added, whilst still stirring vigorously. The mixture was stirred and heated at 110° C. until the solution was virtually neutral to indicator paper, which required from 5 to 6 hours. After concentration in vacuo, the residue was taken up in 250 cm³ of water and the mixture was extracted with chloroform (2×300 cm³). The combined organic extracts were washed with water, dried (MgSO₄) and then concentrated to dryness in vacuo. The residue was recrystallised from isopropanol (100 cm³). 83 g of 7-chloro-3-ethoxy-carbonyl-1-ethyl-6-fluoro-4-oxo-1,4-dihydroquinoline were obtained, which melts in two stages: m.p. 145° C., solidification, followed by m.p. 162° C.

113 g of this ester were saponified by heating under reflux for 1 hour 30 minutes with an aqueous-alcoholic solution of sodium hydroxide (NaOH: 30 g, water: 300 cm³, ethanol: 100 cm³). At the end of the alkaline treatment, the solution was treated with 10 g of animal charcoal, filtered and neutralised by adding 46 cm³ of acetic acid. The precipitate was filtered off, washed with water and recrystallised from DMF (550 cm³). 95 g of 7-chloro-6-fluoro-1-ethyl-4-oxo-1,4-dihydro-quinoline-3-carboxylic acid, m.p. 277° C., were obtained.

EXAMPLE 21

53.9 g of 7-chloro-6-fluoro-1-ethyl-4-oxo-,1,4-dihydro-quinoline-3-carboxylic acid and 80 g of 1-methyl-piperazine, in suspension in 300 cm³ of pyridine, were heated under reflux for 16 hours, whilst stirring. After heating for about one hour, the acid dissolved and the reaction product began to precipitate partially after the second hour. After 14 hours, 93% of the theoretical amount of chlorine was in the ionised form. After cooling, 250 cm³ of water were added to the mixture and the latter was then concentrated to dryness in vacuo (15 mm Hg at 100° C.), in order to remove the pyridine and the excess of methylpiperazine as completely as possible. The residue was taken up in 800 cm³ of water and the mixture was stirred vigorously and treated with acetic acid (55 cm³) in order to dissolve the solid portion. The solution, which was slightly turbid, was treated with 5 g of animal charcoal, stirred for 30 minutes, filtered and then brought to pH 7 by adding 5 N NaOH. After standing overnight at 4° C., the precipitate was filtered off and washed with water and with alcohol. 43.7 g of 1-ethyl-6-fluoro-7-(4-methyl-piperazinyl)-4-oxo-1,4-dihydro-quinoline-3-carboxylic acid, m.p. 270° C., which was identical to the product of Example 20, were obtained.

METHANESULPHONATE 3.33 g of the acid (0.01 mol) were suspended in 50 cm³ of ethanol, the mixture was heated under reflux and 1 g (0.011 mol) of methanesulphonic acid was added thereto. The starting material dissolved and the salt when precipitated. After 5 minutes, the mixture was cooled to 0° C. and the solid was separated and then recrystallised from methanol. 3.8 g of the methane-sulphonate, m.p. 284°–286° C. (decomposition), were obtained.

Analysis for $C_{17}H_{20}FN_3O_3.HO_3SCH_3$(molecular weight 429): Calculated % C 50.03, H 5.63, N 9.78, S 7.45; Found % C 50.49, H 6.04, N 9.55, S 7.39.

EXAMPLE 22

1-Ethyl-6-fluoro-4-oxo-7-piperazinyl-1,4-dihydro-quinoline-3-carboxylic acid 36 g (0.134 mol) of 7-chloro-1-ethyl-6-fluoro-4-oxo-1,4-dihydro-quinoline-3-carboxylic acid, 46 g of piperazine and 210 cm³ of pyridine were heated under reflux for 6 hours, whilst stirring. After the starting material had dissolved, a precipitate appeared after heating for about 2 hours 30 minutes. The major part of the solvent was removed by concentration in vacuo (15 mm Hg;) 100° C.). In order to remove the pyridine as completely as possible, the residue was taken up in 200 cm³ of water and the concentration in vacuo was repeated.

The residue, resuspended in 150 cm³ of water, was stirred. 150 cm³ of 2 N NaOH were added thereto. The solution, which was slightly turbid, was treated with 5 g of animal charcoal and stirred for 30 minutes. After filtration, the pH was brought to 7.2 by adding acetic acid, whilst stirring. The precipitate was filtered off, washed with water and dissolved in 250 cm³ of a 10% aqueous acetic acid. The acid solution (pH 4.4) was filtered and then brought to pH 7.2 by gradually adding 2 N NaOH.

The suspension was heated to 90° C., whilst stirring. The crystals were separated and recrystallised from 280 cm³ of a mixture of DMF (1 volume) and ethanol (4 volumes). After drying in vacuo over phosphorus pentoxide, 29.5 g (yield 70%) of 1-ethyl-6-fluoro-4-oxo-7-piperazinyl-1,4-dihydro-quinoline-3-carboxylic acid, m.p. 222° C., were obtained.

In air, this product is hygroscopic and gives a hemihydrate.

Analysis for $C_{16}H_{18}FN_3O.\frac{1}{2}H_2O$ (molecular weight=319): Calculated % C 58.52, H 5.80, N 12.80; Found % C 58.86, H 5.55, N 12.92.

EXAMPLE 23

7-(4-Allylpiperazinyl)-1-ethyl-6-fluoro-4-oxo-1,4-dihydro-quinoline-3-carboxylic acid 27 g (0.1 mol) of 7-chloro-1-ethyl-6-fluoro-4-oxo-1,4-dihydro-quinoline-3-carboxylic acid, 50 g of 1-allylpiperazine (0.4 mol) and 150 cm³ of DMSO were stirred and heated at 110° C. for 8 hours, during which the reaction product partially precipitated.

After cooling, the mass was taken up in 300 cm³ of water; the precipitate was filtered off, washed with water and recrystallised from 220 cm³ of methylcellosolve.

20.5 g of 7-(4-allylpiperazinyl)-1-ethyl-6-fluoro-4-oxo-1,4-dihydro-quinoline-3-carboxylic acid, m.p.=236° C., were obtained.

Analysis for $C_{19}H_{22}FN_3O_3$(molecular weight 359): Calculated % C 63.50, H 6.13, N 11.69; Found % C 63.83, H 6.22, N 11.12.

Using the procedures described in Examples 21–23, other new compounds have been obtained, the physical constants of which are indicated in Table 1 which follows.

TABLE 1

Structure:

F—[quinoline ring with C=O, COOH at 3-position, N-C₂H₅ at 1-position, R₁R₂N at 7-position]

| Example No. | R₁R₂N | M.P. °C | Solvent and reaction time |
|---|---|---|---|
| 24 | O(CH₂CH₂)₂N— (morpholino) | 259–260(a) | pyridine (14 hours) |
| 25 | H₅C₆CH₂—N(CH₂CH₂)₂N— | 214(b) | DMSO (8 hours) |
| 26 | HOH₂C—CH₂—N(CH₂CH₂)₂N— | 230(c) | DMSO (8 hours) |
| 27 | (azetidine) N— | 348–350(d) | DMSO (8 hours) |
| 28 | (piperidine) N— | 206(d) | DMSO (8 hours) |
| 29 | HO—(pyrrolidinyl)N— | 215(d) | pyridine (9 hours) |
| 30 | OHC—N(CH₂CH₂)₂N— | 285–287(c) | DMSO (8 hours) |

Recrystallisation solvents: (a) DMF; (b) Ethanol (10 volumes) - DMF (1 volume); (c) Ethanol (10 volumes) - DMF (1 volume); (d) Ethanol.

EXAMPLE 31

6-Fluoro-1-methyl-7-(4-methylpiperazinyl)-4-oxo-1,4-dihydro-quinoline-3-carboxylic acid 2.55 g (0.01 mol) of 7-chloro-6-fluoro-1-methyl-4-oxo-1,4-dihydro-quinoline-3-carboxylic acid, 4.5 cm³ of 1-methylpiperazine (0.011 mol) and 32 cm³ of DMSO were heated at 110° C. for 4 hours. After cooling, the mixture was taken up in 150 cm³ of water. The crystalline precipitate was filtered off, washed and recrystallised from 100 cm³ of methylcellosolve. 1.3 g of 6-fluoro-1-methyl-7-(4-methylpiperazinyl)-4-oxo-1,4-dihydroquinoline-3-carboxylic acid, m.p. 304° C. (decomposition), were obtained.

Analysis for $C_{16}H_{18}FN_3O_3$ (molecular weight 319.32): Calculated % C 60.18, H 5.68, N 13.16; Found % C 60.58, H 5.85, N 12.99.

The 7-chloro-6-fluoro-1-methyl-4-oxo-1,4-dihydro-quinoline-3-carboxylic acid used for this synthesis was obtained from the 7-chloro-3-ethoxycarbonyl-6-fluoro-quinoline described in Example 20. 14 g of 7-chloro-3-ethoxycarbonyl-6-fluoroquinoline, 14 g of potassium carbonate and 180 cm³ of DMF were stirred and heated at 110° C. for one hour in a round-bottomed flask equipped with a reflux condenser. After cooling to 50° C., 30 cm³ of methyl iodide were added dropwise. The mixture was stirred and heated at 70°–80° C. until the medium was neutral, which required about 8 hours.

After concentration to dryness in vacuo, the residue was taken up in 100 cm³ of water. The mixture was extracted with chloroform (3×50 cm³) and the combined organic extracts were dried (MgSO₄) and concentrated to dryness in vacuo. The residue was recrystallised from ethanol (200 cm³). 13.5 g of 7-chloro-3-ethoxy-carbonyl-6-fluoro-1-methyl-4-oxo-1,4-dihydroquinoline, m.p. 220° C., were obtained. 5 g of this ester were saponified by heating under reflux for 30 minutes with an aqueous-alcoholic solution of sodium hydroxide (NaOH: 1.4 g, water: 50 cm³, ethanol: 50 cm³). The solution was neutralised with acetic acid(2 cm³). The precipitate was filtered off, washed with water and recrystallised from DMF (55 cm³). 4.05 g of 7-chloro-6-fluoro-1-methyl-4-oxo-1,4-dihydro-quinoline-3-carboxylic acid, m.p. 342° C., were obtained.

EXAMPLE 32

6-Fluoro-1-methyl-4-oxo-7-piperazinyl-1,4-dihydro-quinoline-3-carboxylic acid 2.55 g (0.01 mol) of 7-chloro-6-fluoro-1-methyl-4-oxo-1,4-dihydro-quinoline-3-carboxylic acid and 3.5 g (0.04 mol) of piperazine in 34 cm³ of pyridine were heated under reflux for 7 hours, whilst stirring. The starting materials had completely dissolved in 2 hours and the reaction product began to precipitate in the medium after 4 hours.

The solvent was removed by distillation in vacuo (15 mm Hg) at 100° C. The residue was suspended in 30 cm³ of water and the mixture was stirred vigorously and its pH was brought to 7.5 by gradually adding acetic acid.

The solid was filtered off, washed with water and recrystallised from a mixture of DMF (2 volumes) and ethanol (1 volume). 1.5 g of 6-fluoro-1-methyl-4-oxo-7-piperazinyl-1,4-dihydro-quinoline-3-carboxylic acid, m.p. 310° C. with decomposition, were obtained.

Analysis for $C_{15}H_{16}FN_3O_3$ (molecular weight 305.3): Calculated % C 59.00, H 5.28, N 13.78; Found % C 58.44, H 5.54, N 13.43.

EXAMPLE 33

6-Fluoro-1-methyl-7-morpholino-4-oxo-1,4-dihydro-quinoline-3-carboxylic acid 2.55 (0.01 mol) of 7-chloro-6-fluoro-1-methyl-4-oxo-1,4-dihydro-quinoline-3-carboxylic acid, 3.5 cm³ of morpholine (0.01 mol) and 34 cm³ of DMSO were heated at 110° C. for 7 hours, whilst stirring. The reaction product precipitated after heating for 5 hours. After cooling, the mixture was diluted with water (100 cm³) and the solid was filtered off, washed with water and recrystallised from DMF (45 cm³). 1 g of 6-fluoro-1-methyl-7-morpholino-4-oxo-1,4-dihydro-quinoline-3-carboxylic acid, m.p. 316° C. (decomposition), was obtained.

Analysis for $C_{15}H_{15}FN_2O$ (molecular weight 306.3): Calculated % C 58.78, H 4.93, N 9.14; Found % C 58.42, H 5.17, N 9.29.

EXAMPLE 34

1-Allyl-6-fluoro-7-(4-methylpiperazinyl)-4-oxo-1,4-dihydro-quinoline-3-carboxylic acid 1.4 g of 1-allyl-7-chloro-6-fluoro-4-oxo-1,4-dihydro-quinoline-3-carboxylic acid (0.005 mol), 2.5 cm³ of 1-methyl-piperazine (0.02 mol) and 21 cm³ of pyridine were heated under reflux for 20 hours. The solvent was driven off in vacuo (15 mm Hg) at 100° C. The residue was taken up in 25 cm³ of water and the suspension was stirred and its pH was brought to 7.5 by adding acetic acid. The mixture was extracted with chloroform (4×10 cm³), the combined organic extracts were dried (MgSO₄) and evaporated to dryness and the residue was recrystallised from 10 cm³ of isopropanol.

1 g of 1-allyl-6-fluoro-7-(4-methylpiperazinyl)-4-oxo-1,4-dihydro-quinoline-3-carboxylic acid, m.p. 208° C., was obtained.

Analysis for $C_{18}H_{20}FN_3O_3$ (molecular weight 345.36): Calculated % C 62.59, H 5.84, N 12.17; Found % C 62.28, H 6.00, N 12.15.

The 1-allyl-7-chloro-6-fluoro-4-oxo-1,4-dihydro-quinoline-3-carboxylic acid used in this example, and in those which follow, was prepared from 7-chloro-3-ethoxycarbonyl-6-fluoro-4-hydroxyquinoline:

13.5 g of 7-chloro-3-ethoxycarbonyl-6-fluoro-4-hydroxyquinoline and 13.8 g of potassium carbonate in 160 cm³ of DMF were stirred and heated at 110° C. for 1 hour in a round-bottomed flask equipped with a reflux condenser. After cooling to 60° C., the solution was treated with 24 g of allyl bromide. The mixture was stirred and heated at 100° C. until the medium was neutral (duration: about 6 hours). The solvent was evaporated off in vacuo, the residue was taken up in 300 cm³ of water and the reaction product was extracted with chloroform (3×100 cm³). The combined organic extracts were washed with water, dried (MgSO₄) and evaporated to dryness. The residue was recrystallised from 72 cm³ of isopropanol. 12 g of 1-allyl-7-chloro-3-ethoxycarbonyl-6-fluoro-4-oxo-1,4-dihydroquinoline, m.p.=162°-164° C., were obtained.

9 g of this ester were saponified by heating under reflux for one hour with an aqueous-alcoholic solution of sodium hydroxide (NaOH: 2,9 g, water: 40 cm³, ethanol: 70 cm³). Whilst still hot, the solution was acidified with acetic acid (2.9 cm³). After cooling, the solid was filtered off, washed with water and recrystallised from 40 cm³ of a mixture of DMF (1 volume) and ethanol (1 volume).

6.5 g of 1-allyl-7-chloro-6-fluoro-4-oxo-1,4-dihydro-quinoline-3-carboxylic acid, p.p. 234° C., were obtained.

EXAMPLE 35

1-Allyl-6-fluoro-4-oxo-7-piperazinyl-1,4-dihydro-quinoline-3-carboxylic acid

A mixture of 1-allyl-7-chloro-6-fluoro-4-oxo-1,4-dihydro-quinoline-3-carboxylic acid (2.8 g; 0.01 mol), piperazine (3.5 g; 0.04 mol) and pyridine (20 cm³) was heated under reflux for 20 hours. The solvent was evaporated off in vacuo (15 mm Hg) while heating to 100° C. and the residue was taken up in 30 cm³ of water. The alkaline suspension (pH=9.4) was stirred and adjusted to pH 7.3 by adding acetic acid.

The solid was filtered off and recrystallised from 40 cm³ of a mixture of DMF (1 volume) and ethanol (5 volumes). 1.4 g of 1-allyl-6-fluoro-4-oxo-7-piperazinyl-1,4-dihydro-quinoline-3-carboxylic acid, m.p. 136° C., were obtained, which, in air, fixes one molecule of water (hydrate, m.p. 142° C.).

Analysis for $C_{17}H_{18}FN_3O_3 \cdot H_2O$ (molecular weight 349.3): Calculated % C 58.44, H 5.56, N 12.03; Found % C 58.41, H 5.56, N, 12.45.

EXAMPLE 36

1-Allyl-6-fluoro-7-[4-(β-hydroxyethyl)-piperazinyl-4-oxo-1,4-dihydro-quinoline-3-carboxylic acid This acid was obtained by the procedure described in Example 35, but replacing the piperazine with the equivalent amount of 1-(β-hydroxyethyl)-piperazine (5.2 cm³). The crude product was recrystallised from 20 cm³ of isopropanol and had a m.p. of 171° C. Yield 1.5 g.

Analysis for $C_{19}H_{22}FN_3O_4$ (molecular weight 375.38): Calculated % C 60.80, H 6.18, N 11.13; Found: % C 60.92, H 6.15, N 10.97.

EXAMPLE 37

1-Allyl-7-(4-allylpiperazinyl)-6-fluoro-4-oxo-1,4-dihydro-quinoline-3-carboxylic acid This acid was prepared by the procedure of Example 35, but replacing the piperazine with the equivalent amount (6.05 g) of 1-allylpiperazine. The crude product was recrystallised from ethanol (20 cm³). Yield: 1.5 g, m.p. 186° C.

Analysis for $C_{20}H_{22}FN_3O_3$ (molecular weight 371): Calculated % C 64.67, H 5.96, N 11.15; Found % C 64.90, H 6.14, N 11.28.

EXAMPLE 38

1-Allyl-7-(4-benzylpiperazinyl)-6-fluoro-4-oxo-1,4-dihydro-quinoline-3-carboxylic acid 2.8 g (0.01 mol) of 1-allyl-7-chloro-6-fluoro-4-oxo-1,4-dihydro-quinoline-3-carboxylic acid, 7.2 g (0.04 mol) of 4-benzylpiperzine and 15 cm³ of DMSO were stirred and heated at 110° C. for 6 hours. The solvent was removed by distillation in vacuo. The residue was taken up in 40 cm³ of water. The suspension was adjusted to pH 7.3 by adding acetic acid. The precipitate was extracted with chloroform (4×20 cm³). The combined organic extracts were washed with water and then evaporated to dryness to give a viscous residue which crystallized on mixing with 10 cm³ of isopropanol. The solid was separated and recrystallised from methylcellosolve (30 cm³). 1.5 g of the acid, m.p. 209° C., were obtained.

Analysis for $C_{24}H_{24}FN_3O_3$ (molecular weight 421.45): Calculated % C 68.42, H 5.73, N 9.97; Found % C 68.58, H 5.91, N 9.90.

EXAMPLE 39

1-Allyl-6-fluoro-7-morpholino-4-oxo-1,4-dihydro-quinoline-3-carboxylic acid 1.4 g (0.005 mol) of 1-allyl-7-chloro-6fluoro-4-oxo-1,4-dihydro-quinoline-3-carboxylic acid and 1.75 cm³ of morpholino in 22 cm³ of pyridine were heated under reflux for 20 hours. The reaction product was isolated as indicated in Example 35 and purified by recrystallisation from methylcellosolve (25 cm³). Yield: 1 g (63%), m.p. 210° C.

Analysis for $C_{17}H_{17}FN_2O_4$ (molecular weight 332.33): Calculated % C 61.43, H 5.15, N 8.43; Found % C 61.45, H 5.24, N 8.29.

EXAMPLE 40

1-Benzyl-6-fluoro-7-(4-methylpiperazinyl)-4-oxo-1,4-dihydro-quinoline-3-carboxylic acid 1.65 g (0.005 mol) of 1-benzyl-7-chloro-6-fluoro-4-oxo-1,4-dihydro-quinoline-3-carboxylic acid, 2.5 cm³ of 1-methylpiperazine and 12 cm³ of pyridine were heated under reflux for 9 hours. The reaction product was isolated as indicated in Example 35 and purified by recrystallisation from methylcellosolve (20 cm³). 1 g of 1-benzyl-6-fluoro-7-(4-methylpiperazinyl)-4-oxo-1,4- dihydro-quinoline-3-carboxylic acid, m.p. 266° C., was obtained.

Analysis for $C_{22}H_{22}FN_3O_3$ (molecular weight 384.32): Calculated % C 66.83, H 5.56, N 10.68; Found % C 66.95, H 5.85, N 10.33.

The 1-benzyl-7-chloro-6-fluoro-4-oxo-1,4-dihydroquinoline-3-carboxylic acid was prepared from 7-chloro-3-ethoxy-carbonyl-6-fluoro-4-hydroxyquinoline:

16.2 g of 7-chloro-3-ethoxycarbonyl-6-fluoro-4-hydroxyquinoline, 16.8 g of potassium carbonate and 150 cm³ of DMF were heated for one hour, whilst stirring, in a round-bottomed flask equipped with a reflux condenser. 27.5 cm³ of benzyl chloride were added and the heating and stirring were maintained until the pH of the medium was neutral, which required about 2 hours. The major part of the solvent was removed by distillation in vacuo (15 mm Hg) at 100° C. The residue was taken up in 300 cm³ of water. The mixture was extracted with 3×100 cm³ of chloroform. The combined organic extracts were washed with water, dried (MgSO₄) and evaporated to dryness. The residue was recrystallised from methylcellosolve. 17.5 g (81%) of 1-benzyl-7-chloro-3-ethoxycarbonyl-6-fluoroquinoline, m.p. 211°-212° C., were obtained.

17.5 g. of this ester were saponified by heating and stirring for one hour with an aqueous-alcoholic solution of sodium hydroxide (NaOH: 3.9 g, water: 75 cm³, ethanol: 50 cm³). The salt which had partially precipitated was dissolved by adding 150 cm³ of water. The solution was treated with 6 cm³ of acetic acid.

The precipitate was filtered off, washed with water and recrystallised from 170 cm³ of methylcellosolve. 15.4 g of 1-benzyl-7-chloro-6-fluoro-4-oxo-1,4-dihydroquinoline-3-carboxylic acid, m.p. 250° C., were obtained.

EXAMPLE 41

6-Fluoro-7-(4-methyl-piperazinyl)-4-oxo-1-vinyl-1,4-dihydro-quinoline-3-carboxylic acid (Process A)

A solution of 1.3 g of 7-chloro-6-fluoro-4-oxo-1-vinyl-1,4-dihydro-quinoline-3-carboxylic acid and 2.5 cm³ of 1-methyl-piperazine in 13 cm³ of pyridine was heated for 17 hours under reflux. The reaction mixture was concentrated to dryness under reduced pressure and the residue was taken up in 10 cm³ of N NaOH. The solution obtained, which had a deep brown colour, was heated and agitated with animal charcoal (0.5 g). After filtration, the pH of the solution was adjusted to 7 by the addition of acetic acid, then extracted with chloroform (4×10 cm³). The combined organic extracts were evaporated to dryness and the residue was recrystallised from ethanol. The product, 6-fluoro-7-(4-methyl-piperazinyl)-4-oxo-1-vinyl-1,4-dihydro-quinoline-3-carboxylic acid, had m.p. 242° C.

Analysis for $C_{17}H_{18}FN_3O_3$ (molecular weight 331.3): Calculated % C 61.59, H 5.47, N 12.68; Found % C 61.38, H 5.66, N 12.51.

The starting material for this process, 7-chloro-6-fluoro-4-oxo-1-vinyl-1,4-dihydro-quinoline-3-carboxylic acid, was obtained as follows:

A solution of 8.1 g of 7-chloro-3-ethoxycarbonyl-6-fluoro-4-oxo-1,4-dihydro-quinoline and 8.2 g of potassium carbonate in 70 cm³ of DMF was agitated and heated at 110° C. for 1 hour. After cooling to 60° C., 15 of 2-bromo-ethanol were added to the reaction mixture and it was agitated and heated at 110° C. for 4 hours. After evaporation of the solvent under reduced pressure, 100 cm³ of water were added to the residue and the aqueous mixture was extracted with chloroform (4×100 cm³). The combined organic extracts were washed with water (2×100 cm³), dried over Na₂SO₄, filtered and then evaporated to dryness. The residue was recrystallised from ethanol (150 cm³). 6.75 g of 7-chloro-6-fluoro-3-ethoxycarbonyl-1-(2-hydroxyethyl)-4-oxo-1,4-dihydroquinoline, m.p. 202° C., were obtained; yield 67%.

27 g of the foregoing ester product were added, portionwise, to an agitated and cooled solution of pyridine (8.1 cm³) in thionyl chloride (54 cm³). The addition was carried out at such a rate that the temperature of the mixture remained between 0° and 5° C. After returning to room temperature, the solution was heated for 1 hour under reflux and the excess of reagent was then removed by distillation under reduced pressure. The residue was added, with agitation, to 100 cm³ of iced water. The suspension obtained was neutralised by the addition of 10% aqueous Na₂CO₃. The precipitate obtained was filtered off, washed with water and recrystallised from ethanol (480 cm³). 22.4 g of 7-chloro-1-(2-chloroethyl)-3-ethoxycarbonyl-6-fluoro-4-oxo-1,4-dihydro-quinoline, m.p. 222° C., were obtained; yield 80%.

5.9 g of this ester product were added to an aqueous alcoholic solution of caustic soda (8.5 g NaOH, 80 cm³ water, 30 cm³ ethanol). The mixture was heated for 2 hours under reflux. After dissolution of the ester, the sodium salt of the product formed was precipitated. It was dissolved by the addition of water (50 cm³) while maintaining reflux temperature. The solution was acidified with hydrochloric acid, the precipitate obtained was filtered off and washed with water and then with ethanol. 4.8 g of 7-chloro-6-fluoro-4-oxo-1-vinyl-1,4-dihydro-quinoline-3-carboxylic acid, m.p. 210°, were obtained.

EXAMPLE 42

6-Fluoro-7-morpholino-4-oxo-1-vinyl-1,4-dihydroquinoline-3-carboxylic acid 2.6 g of 7-chloro-6-fluoro-4-oxo-1-vinyl-1,4-dihydroquinoline-3-carboxylic acid, 3.5 cm3 of morpholine and 30 cm³ of dimethylsulphoxide were heated for 15 hours under reflux. The solvent was removed by distillation under reduced pressure and the residue was taken up in 20 cm³ of ethanol. The insoluble solid was separated and recrystallised from 8 cm³ of a 1:1 (by volume) mixture of methylcellosolve and ethanol. 0.4 g of 6-fluoro-7-morpholino-4-oxo-1-vinyl-1,4-dihydroquinoline-3-carboxylic acid, m.p. 218°-220° C., was obtained.

Analysis for $C_{16}H_{15}FN_2O_4$ (molecular weight 318.29): Calculated % C 60.37, H 4.75, N 8.79; Found % C 60.37, H 4.98, N 8.62.

EXAMPLE 43

6-Fluoro-7-(4-methyl-piperazinyl)-4-oxo-1-vinyl-1,4-dihydro-quinoline-3-carboxylic acid Process B (a) 28 g of 7-chloro-6-fluoro-1-(2-hydroxyethyl)-4-oxo-1,4-dihydro-quinoline-3-carboxylic acid, 40 g of 1-methyl piperazine and 200 cm³ of pyridine were heated for 18 hours under reflux. The solvent was removed by distillation under reduced pressure. The residue was taken up in 100 cm³ of water, the mixture was agitated and adjusted to pH 6.8 by the addition of acetic acid. The solid was filtered off, washed with water and recrystallised from DMF. 24 g of 6-fluoro-1-(2-hydroxyethyl)-7-(4-methyl-piperazinyl)-4-oxo-1,4-dihydroquinoline-3-carboxylic acid, m.p. 270° C., were obtained.

Analysis for $C_{17}H_{20}FN_3O_4$ (molecular weight 349.35): Calculated % C 58.44, H 5.76, N 12.02; Found % C 58.58, H 5.95, N 11.91.

(b) 8.75 g (0.025 mole) of the preceding acid were added, in small portions, to 75 cm$^3$ of thionyl chloride while the latter was agitated and externally cooled. The addition was carried out at such a rate that the temperature of the mixture was maintained between 0° and 5° C. 2 cm$^3$ (0.025 mole) of pyridine were then added. After returning to room temperature, the mixture was heated under reflux for 5 hours. The excess of thionyl chloride was removed by evaporation under reduced pressure. The residue was added to 60 cm$^3$ of ethanol. The solution obtained was agitated for 15 minutes at room temperature. The solvent was evaporated under reduced pressure and the residue was taken up in 100 cm$^3$ of water. The mixture was agitated and adjusted to pH 7 by the addition of 10% aqueous $Na_2CO_3$ solution. The precipitate was filtered off, washed with iced water and dried under reduced pressure. 7 g of 1-(2-chloroethyl)-3-ethoxycarbonyl-6-fluoro-7-(4-methylpiperazinyl)-4-oxo-1,4-dihydro-quinoline were obtained; yield 70%. The product was purified by recrystallisation from 80 cm$^3$ of a 1:1 (by volume) mixture of ethanol and isopropyl oxide; m.p. 208° C.

In damp air, this ester forms a hydrate containing ½ molecule of water.

Analysis for $C_{19}H_{23}ClFN_3O_3$, ½ $H_2O$ (molecular weight 404.86): Calculated % C 56.38, H 5.93, N 10.38; Found % C 55.95 H 5.69, N 10.02.

(c) 6 g of the ester product of b) were added to an aqueous alcoholic solution of caustic soda (6.5 g NaOH, 45 cm$^3$ water, 25 cm$^3$ ethanol). The mixture was heated under reflux for 2 hours; the sodium salt of the reaction product partially precipitated. The solvents were eliminated under reduced pressure. The residue was taken up in 50 cm$^3$ of water. The suspension was vigorously agitated and adjusted to pH 6.8 by the addition of acetic acid. After standing overnight at 4° C., the solid which had precipitated was filtered off, washed with iced water and dried over phosphoric anhydride under reduced pressure. 4 g of 6-fluoro-7-(4-methylpiperazinyl)-4-oxo-1-vinyl-1,4-dihydro-quinoline-3-carboxylic acid were obtained; yield 80%. The product was purified by recrystallisation from 100 cm$^3$ of methyl cellosolve; m.p. 242° C., identical to the product described in Example 21.

The antimicrobial activity of the compounds according to the invention has been investigated in vitro on Gram positive and Gram negative bacteria using, as the culture medium, nutrient agar (N.A.) of the following formulation:

meat extract: 3 g
peptone: 5 g
agar: 15 g
Water q.s.p.: 1,000 cm$^3$

After sterilisation at 120° C., the pH was 6.8.

The minimum inhibitory concentrations (M.I.C.) were determined by dilution of the test compounds in this mixture, the concentration ranging from 0.05 to 100 µg/cm$^3$ in a geometric progression with a factor of 2.

The inoculation of the dishes was carried out by means of a multiple inoculator with $10^{-3}$ dilutions of 18 hour old broth cultures.

The dishes were placed in an oven at 37° C. and the readings were taken afer an incubation time of 18 hours. The M.I.C. was taken as the lowest concentration which inhibited a culture.

Table 2 gives the M.I.C. of the compounds of the invention containing a chlorine atom in the 6-position against 5 Gram positive bacteria (from 1 to 5) and 17 Gram negative bacteria (from 6 to 22).

The activities of the corresponding acids which do not contain a halogen substituent in the 6-position are also shown, for purpose of comparison, for certain of the compounds studied, especially those of Examples 1 and 4. These comparison compounds are denoted $T_1$ and $T_4$ respectively.

Examination of Table 2 shows the importance of the chlorine atom in the activity of the compounds of the invention and the superiority of the latter over their non-halogenated homologues.

The following compounds are specially singled out, because of their broad spectrum of activity, as being useful for therapeutic applications in human or veterinary medicine:

Example 1—6-chloro-1-ethyl-7-(4-methylpiperazinyl)-4-oxo-1,4-dihdro-quinoline-3-carboxylic acid Example 3—6-chloro-1-ethyl-4-oxo-7-piperazinyl-1,4-dihydro-quinoline-3-carboxylic acid.

TABLE 2

| | | Ex. 1 | $T_1$ | Ex. 3 | Ex. 4 | $T_4$ | Ex. 5 | Ex. 7 |
|---|---|---|---|---|---|---|---|---|
| | | (M.I.C. in µg/cm$^3$) | | | | | | |
| 1 | Staph. 209 P | 0.4 | 3.1 | 0.4–0.8 | 0.4 | 6.2 | 0.2 | 0.2 |
| 2 | Staph. 9.144 | 0.4–1.6 | 6.2 | 0.4 | 0.4 | 3.1 | 0.8 | 0.4 |
| 3 | Strepto A 561 | 12.5–50 | 50 | 6.2 | 6.2 | >100 | 6.2 | 100 |
| 4 | Strepto D.M. 19 | 1.6–3.1 | 50 | 1.6–3.1 | 6.2 | 100 | 6.2 | 50 |
| 5 | B. subtilis | 0.2–0.4 | 1.6 | 0.2–0.4 | 6.2 | 3.1 | 0.4 | 0.2 |
| 6 | Bord. bronchis. 4.617 | 1.6–6.2 | 25 | 0.2–12.5 | 6.2 | 100 | 12.5 | 12.5 |
| 7 | Ps. aeuruginosa A.22 | 3.1–6.2 | 12.5 | 1.6–3.1 | 12.5 | 100 | 25 | 12.5 |
| 8 | Ps. aeruginosa 72.345 | 3.1–6.2 | 12.5 | 1.6–3.1 | 12.5 | 100 | 25 | 6.2 |
| 9 | Esch. coli 95 I.S.M. | 0.4–0.8 | 0.8 | 0.2 | 1.6 | 6.2. | 3.1 | 1.6 |
| 10 | Esch. coli 54.127 O.M.S. | 0.2–0.4 | 1.6 | 0.2 | 3.1 | 6.2 | 6.2 | 3.1 |
| 11 | Esch. coli 111 B4 | 0.2–0.4 | 1.6 | 0.2 | 3.1 | 6.2 | 3.1 | 3.1 |
| 12 | Klebs. pneum. 10.031 | 0.2 | 0.8 | 0.2 | 0.4 | 3.1 | 0.4 | 0.2 |
| 13 | Salm. typhi 0901 | 0.4–1.6 | 3.1 | 0.2 | 3.1 | 25 | 6.2 | 3.1 |
| 14 | S. enteritidis Danysz | 0.4–1.6 | 3.1 | 0.2 | 3.1 | 12.5 | 6.2 | 3.1 |
| 15 | S. oranienburg 1066 | 12.5–25 | >100 | 6.2–12.5 | 25 | >100 | 100 | >100 |
| 16 | Arizona 6.211 | 0.2–0.8 | 1.6 | 0.2 | 1.6 | 12.5 | 3.1 | 1.6 |
| 17 | Berratia | 1.6–3.1 | 12.5 | 3.1–12.5 | 25 | >100 | 3.1 | 0.8 |
| 18 | Providentia 0223 | 3.1–12.5 | 100 | 1.6–3.1 | 25 | >100 | 50 | >100 |
| 19 | Sh. sonnei I.P.S. | 0.2–0.85 | 1.6 | 0.2 | 0.8 | 6.2 | 1.6 | 0.8 |
| 20 | Pr. vulgaris 12–53 | 0.4–1.6 | 3.1 | 0.2 | 1.6 | 25 | 6.2 | 0.8 |
| 21 | Pr. mirabilis Nig | 0.4–0.8 | 3.1 | 0.2 | 3.1 | 50 | 6.2 | 1.6 |

TABLE 2-continued

| | (M.I.C. in $\mu g/cm^3$) | | | | | | |
|---|---|---|---|---|---|---|---|
| | Ex. 1 | $T_1$ | Ex. 3 | Ex. 4 | $T_4$ | Ex. 5 | Ex. 7 |
| 22 Pr. morganii A.236 | 0.2–0.8 | 0.8 | 0.2 | 1.6 | 3.1 | 3.1 | 0.8 |

In vitro, the fluorine-containing compounds described in Examples 20 to 42 have anti-bacterial properties which are even more marked than those of their chlorine-containing homologues, as shown in Table 3 in which the activities of the most active acids are compared with those of oxolinic acid.

it is also evident from this table that the acids containing a fluorine atom in the 6-position are compounds having a broad spectrum, the anti-bacterial activities of which compounds, especially with respect to Proteus, Klebsiella, Serratia and Providentia, can be valuable in human and veterinary medicine.

The products of the following examples are especially singled out:

Example 20 1-Ethyl-6-fluoro-7-(4-methyl-piperazinyl)-4-oxo-1,4-dihydro-quinoline-3-carboxylic acid.

Example 22 1-Ethyl-6-fluoro-4-oxo-7-piperazinyl-1,4-dihydro-quinoline-3-carboxylic acid.

Example 23 7-(4-Allylpiperazinyl)-1-ethyl-6-fluoro-4-oxo-1,4-dihydro-quinoline-3-carboxylic acid.

EXAMPLE 41

6-Fluoro-7-(4-methyl-piperazinyl)-4-oxo-1-vinyl-1,4-dihydro-quinoline-3-carboxylic acid These compounds have a remarkably low toxicity, as shown by the results recorded in Table 4 in which the 50% lethal dose ($LD_{50}$) for mice are indicated, when the products are administered intravenously (i.v.) or orally (p.o.).

The activity of the compounds according to the invention against systemic infections in mice, caused by Staphylococcus 50,774, Streptococcus pyogenes A 65, Pseudomonas aeruginosa No. 12 and Escherichia coli P 5101, has been studied.

The infections were set up by intraperitoneal injection of a suspension of the bacterial culture corresponding to the germ studied. The products were administered orally at the time of injection, and 6 hours later. The mortality was observed for 14 days for Staph. Aureus and for 7 days for the other germs.

The 50% effective dose ($ED_{50}$) which protects 50% of the animals from death caused by the infection, and the $ED_{90}$ which protects 90% of the animals, were thus determined. Oxolinic acid was used as the reference substance.

In these experiments, the 6-fluoroacids were the most effective and, amongst these, those of Examples 20, 22 and 23 are preferred, as shown in Table 4 in which the minimum inhibitory concentrations (M.I.C.) of each of the compounds are also indicated for the germs used in the experimental infections. These three products have a very substantially greater activity than oxolinic acid in the models studied.

TABLE III

| | (M.I.C. $\mu/cm^3$) | | | | | | | | |
|---|---|---|---|---|---|---|---|---|---|
| | Ex. 20 | Ex. 22 | Ex. 23 | Ex. 31 | Ex. 32 | Ex. 34 | Ex. 41 | Ex. 42 | Oxolinic acid |
| 1 Staph. 209 P | 0.2 | 0.2–0.4 | 0.1–0.2 | 0.4 | 0.8 | 0.8 | 0.1 | 0.8 | 0.8 |
| 2 Staph. 9.144 | 0.2 | 0.2–0.4 | 0.2 | 0.4 | 0.8 | 1.6 | 0.2 | 1.6 | 0.8 |
| 3 Strepto A 561 | 0.8–3.1 | 50 | 1.6–6.2 | 12.5 | 6.2–12.5 | 50 | 12.5 | 25 | |
| 4 Strepto D.M. 19 | 0.8–1.6 | 1.6–3.1 | 0.8–3.15 | 3.1–6.2 | 12.5 | 6.2–12.5 | 3.1 | 12.5 | 25 |
| 5 B. Subtilis | 0.05–0.1 | 0.2 | 0.1–0.2 | 0.8 | 0.4 | 0.4 | 0.1 | 0.2 | 0.1 |
| 6 Bord. bronchis. 4.617 | 0.8–3.1 | 6.25–12.5 | 3.12 | 6.25 | 6.25 | 0.2 | 1.6 | 12.5 | 3.1 |
| 7 Ps. aeruginosa A.22 | 0.8 | 0.4–0.8 | 1.6–3.12 | 1.6 | 0.8–3.12 | 3.1 | 0.4 | 3.1 | 12.5 |
| 8 Pd. aeruginosa 72.345 | 0.8 | 0.4–0.8 | 3.12 | 1.6 | 0.4–3.12 | 3.1 | 0.8 | 6.2 | 6.2 |
| 9 Esch. coli 95 I.S.M. | 0.1 | 0.2 | 0.1–0.4 | 0.1 | 0.2 | 0.4 | 0.1 | 0.8 | 0.1 |
| 10 Esch. coli 54.127 O.M.S. | 0.1 | 0.2 | 0.1–0.8 | 0.8 | 0.2 | 0.4 | 0.1 | 0.8 | 0.4 |
| 11 Esch. coli 111 $B_4$ | 0.05–0.1 | 0.1–0.2 | 0.2–0.8 | 0.8 | 0.2 | 0.4 | 0.1 | 0.8 | 0.4 |
| 12 Klebs. pneum. 10.031 | 0.05–0.1 | 0.1–0.2 | 0.1–0.2 | 0.8 | 0.1 | 0.1 | 0.1 | 0.8 | 0.1 |
| 13 Salm. typhi 0901 | 0.1 | 0.05–0.2 | 0.1–0.4 | 0.4 | 0.8 | 0.1 | 0.1 | 0.8 | 0.4 |
| 14 S. enteritidis Danysz | 0.1–0.2 | 0.2 | 0.4 | 0.4 | 0.2 | 0.4–0.8 | 0.1 | 1.6 | 0.8 |
| 15 S. oranienburg 1066 | 3.1 | 6.2 | 6.2–12.5 | 6.2–12.5 | 12.5 | 12.5 | 1.6 | 100 | 25 |
| 16 Arizona 6.211 | 0.1–0.2 | 0.2 | 0.2–0.8 | 0.2–0.4 | 0.2 | 0.4 | 0.1 | 0.8 | 0.4 |
| 17 Serratia | 0.8 | 1–6.2 | 0.025 | 0.2 | 0.2 | 0.05–0.4 | 0.4 | 3.1 | 0.8 |
| 18 Providentia 0223 | 0.8–1.6 | 0.8–1.6 | 1.6–6.2 | 0.8–1.6 | 1.6 | 12.5 | 0.8 | 25 | 25 |
| 19 Sh. sonnei I.P.S. | 0.01–0.02 | 0.01–0.02 | 0.1–0.2 | 0.2–0.4 | 0.1 | 0.2 | 0.1 | 0.8 | 0.2 |
| 20 Pr. vulgaris 12–53 | 0.1–0.4 | 0.05 | 0.2–0.4 | 0.2 | 0.2 | 0.2 | 0.05 | 0.8 | 0.05 |
| 21 Pr. mirabilis Nig | 0.2–0.4 | 0.1–0.2 | 0.4–0.8 | 0.4 | 0.2 | 0.8–1.6 | 0.05 | 1.6 | 0.4 |
| 22 Pr. morganii A. 236 | 0.1–0.4 | 0.05 | 0.2 | 0.2 | 0.2 | 0.05–0.2 | 0.05 | 0.2 | 0.1 |

TABLE 4

| Example | Staph. aureus 50,774 (mg/kg) | | Strept. pyogenes A. 65 (mg/kg) | | P. aeruginosa No. 12 (mg/kg) | | E. coli P 5101 (mg/kg) | | $LD_{50}$ (mg/kg) |
|---|---|---|---|---|---|---|---|---|---|
| | $ED_{90}$ | $ED_{50}$ | $ED_{90}$ | $ED_{50}$ | $ED_{90}$ | $ED_{50}$ | $ED_{90}$ | $ED_{50}$ | |
| Example 20 | 9.3 | 2.9 | 103.3 | 65 | 11.5 | 7.8 | 2.8 | 1.8 | i.v.:350 |
| M.I.C. | 0.39 $\mu g/cm^3$ | | 3.13 $\mu g/cm^3$ | | 1.56 $\mu g/cm^3$ | | 0.1 $\mu g/cm^3$ | | p.o. >2,000 |
| Example 22 | 44.1 | 20.6 | >100 | >100 | 25.9 | 17.7 | 10.4 | 4 | i.v.:354 |
| M.I.C. | 0.78 $\mu g/cm^3$ | | 1.56 $\mu g/cm^3$ | | 0.78 $\mu g/cm^3$ | | 0.1 $\mu g/cm^3$ | | p.o >2,000 |
| Example 23 | 17 | 5.2 | 129.6 | 64.7 | 26.9 | 13.3 | 5.2 | 2.9 | i.v.:177 |
| M.I.C. | 0.39 $\mu g/cm^3$ | | 3.13 $\mu g/cm^3$ | | 6.25 $\mu g/cm^3$ | | 0.39 $\mu g/cm^3$ | | p.o. >2,000 |

TABLE 4-continued

| Example | Staph. aureus 50,774 (mg/kg) | | Strept. pyogenes A. 65 (mg/kg) | | P. aeruginosa No. 12 (mg/kg) | | E. coli P 5101 (mg/kg) | | LD$_{50}$ (mg/kg) |
|---|---|---|---|---|---|---|---|---|---|
| | ED$_{90}$ | ED$_{50}$ | ED$_{90}$ | ED$_{50}$ | ED$_{90}$ | ED$_{50}$ | ED$_{90}$ | ED$_{50}$ | |
| Oxolinic acid | 110.7 | 53.2 | >100 | >100 | 142 | 70.1 | 45.1 | 17.0 | i.v.:177 |
| M.I.C. | 1.56 μg/cm$^3$ | | 100 μg/μg/cm$^3$ | | 12.5 μg/cm$^3$ | | 0.2 μkg/cm$^3$ | | p.o. >2,000 |

The compound of Example 20, 1-ethyl-6-fluoro-7-(4-methylpiperazinyl)-4-oxo-1,4-dihydro-quinoline-3-carboxylic acid, appears to be the most valuable because of its good bacteriological activity and its very low toxicity. In dogs, this product was very well tolerated on oral administration: the administration of a dose of 50 mg/kg did not cause any digestive disorder or any disorder of central nervous origin.

During experiments of this type, the blood of three dogs (A, B and C), which had received the above-mentioned dose by oral administration, was sampled over a period of time and the proportion of active compound was determined bacteriologically by means of *Bacillus subtilis* ATCC 6633. Table 5 gives the concentrations found as well as that for an animal (D) which had also received 25 mg of the compound of Example 20 by oral administration.

TABLE 5

| Dose p.o. | Concentrations in μg/cm$^3$ of plasma after: | | | | | | | | |
|---|---|---|---|---|---|---|---|---|---|
| | 0.5 hour | 1 hour | 2 hours | 3 hours | 4 hours | 6 hours | 8 hours | 10 hours | 24 hours |
| 50 mg/kg A | 2.6 | 3.4 | 7.7 | 10.8 | 9.8 | 8.4 | 6.4 | 5.1 | 2 |
| B | 4.6 | 19.2 | 23.4 | 20.6 | 18 | 13.2 | 8.8 | 4.5 | 0.3 |
| C | | | 4.4 | 11.2 | 17.2 | 16.4 | 10.4 | 6.2 | 0.8 |
| 25 mg/kg D | 2.6 | 7.2 | 7.8 | 6.5 | 6.1 | 4.1 | 2.7 | 1.6 | 0.1 |

As is frequently the case in this type of experiment, the individual variations were noted from animal to animal, but the plasma concentrations observed, during at least the first six hours, were compatible in all cases with the treatment of a systemic complaint caused by most of the bacteria studied.

The urine of the three animals (A, B and C) after 24 hours also had concentrations (c) which were very much greater than the minimum inhibitory concentrations: A (c=54.4 μg/cm$^3$), B (c=72 μg/cm$^3$) and C (c=61 μg/cm$^3$).

All these results make it possible to anticipate a good therapeutic action of the compounds of Examples 20, 22 and 23, and more particularly of the first: 1-ethyl-6-fluoro-7-(4-methylpiperazinyl)-4-oxo-1,4-dihydro-quinoline-3-carboxylic acid.

The compounds according to the invention can be used in human and veterinary medicine for the treatment of systemic or localised infectious diseases, such as infections of the urinary or bile ducts.

In general, a daily dosage of 10 to 60 mg of the active compound per kg body weight is recommended for the treatment of infections caused by sensitive bacteria.

The daily dose can be divided into two, three or four administrations. Compositions containing the active compounds can be administered orally or by injection in a dose falling within the above range. The dosage may, of course, be varied according to the seriousness of the disease treated, and also as a function of age, sex, body weight and the species of animal concerned.

The compounds according to the invention are used as the free bases or as their physiologically acceptable acid addition salts in pharmaceutical compositions which additionally comprise an inert physiologically acceptable carrier. The carrier may be liquid or solid, organic or inorganic, and suitable for oral or parenteral administration and should be inert in the sense of not reacting with the active compounds. Suitable carriers are, for example, water, gelatine, lactose, starch, stearyl alcohol, magnesium stearate, talc, vegetable oils, benzyl alcohol, gums, propylene glycol and petroleum jelly.

For oral administration, suitable forms of pharmaceutical composition are, for example, compressed tablets, dragees, capsules, pills and suspensions. In solid forms, for example capsules and compressed tablets, each dosage unit preferably contains 0.1 to 0.5 g of active compound and 0.1 to 0.5 g of carrier. Suitable carriers for such solid forms are, for example, lactose, starch, talc, gelatine and magnesium stearate.

Aqueous suspensions preferably contain 20 to 100 mg of active compound per cm$^3$. Water soluble high molecular weight compounds may be included in such suspensions in order to stabilise them, such as cellulose esters and polyethylene glycols. Sweetening agents, aromatising agents and/or colourants may also be added.

Injectable compositions preferably comprise solutions of the physiologically acceptable acid addition salts according to the invention in distilled water, the solutions containing from 0.2 to 1 g of the active compound per 5 or 10 cm$^3$ of the final solution. If desired, such solutions may contain the necessary quantity of sodium chloride to render the solution isotonic. The solutions can be presented in 5 or 10 cm$^3$ ampoules which are sterilised in an autoclave. Equally, after sterile filtration, 5 or 10 cm$^3$ of the solution can be filled into the appropriate sized sterile ampoules and then subjected to lyophilisation.

Solutions such as just described can also be used for local treatments in oto-rhino-laryngology or ophthalmology, For this purpose they should be sterilised and may contain adjuvants, such as preservative agents, softening agents, emulsifiers, solubilisers, stabilisers, salts for controlling the osmotic pressure, and buffers.

The compounds according to the invention can, as already stated, be used in veterinary medicine, for example in the forms described above or as additives in animal feedstuffs.

I claim:

1. A compound of formula:

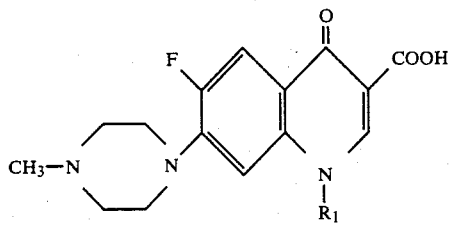

in which

R$_1$ is a methyl, ethyl, vinyl or allyl group and its physiologically acceptable non-toxic acid addition salts thereof.

2. 6-fluoro-1-ethyl-7-(4-methyl piperazinyl)-4-oxo-1,4-dihydro-quinoline-3-carboxylic acid and its physiologically acceptable acid addition salts.

3. 6-fluoro-1-vinyl-7-(4-methyl piperazinyl)-4-oxo-1,4-dihydro-quinoline-3 carboxylic acid and its physiologically acceptable acid addition salts.

4. 6-fluoro-1-methyl-7-(4-methyl piperazinyl)-4-oxo-1,4-dihydro-quinoline-3 carboxylic acid and its physiologically acceptable acid addition salts.

5. 6-fluoro-1-allyl-7-(4-methyl piperazinyl)-4-oxo-1,4-dihydro-quinoline-3 carboxylic acid and its physiologically acceptable acid addition salts.

6. 6-fluoro-1-ethyl-7-(4-methyl-1-piperazinyl)-4-oxo-1,4-dihydroquinoline-3-carboxylic acid, methane sulphonate salt.

7. An anti-bacterial pharmaceutical composition comprising at least one active compound according to any of claims 1, 2, 3, 4 or 5 present in a pharmaceutically effective amount and in admixture with an inert, physiologically acceptable carrier.

8. A composition according to claim 7 in dosage unit form suitable for oral administration, each dosage unit containing from 0.1 to 0.5 g of the active compound.

9. A composition according to claim 7 in dosage unit form suitable for parenteral administration, each dosage unit containing from 0.2 to 1 g of the active compound.

10. Method for the treatment of systemic or localized infection by gram positive or gram negative bacteria wherein an effective quantity of a compound of claims 1, 2, 3, 4 or 5, is administered to a patient suffering from this infection.

11. The method, as defined in claim 10, wherein the infection is of the urinary system in a hot blooded animal.

12. The method, as defined in claim 10, wherein the infection is of the bile duct of a hot blooded animal.

* * * * *